(12) United States Patent
Bodden et al.

(10) Patent No.: US 6,391,102 B1
(45) Date of Patent: May 21, 2002

(54) AIR FILTRATION SYSTEM WITH FILTER EFFICIENCY MANAGEMENT

(75) Inventors: Steven A. Bodden, Redlands; Johann M. Kreutzer, Cherry Valley, both of CA (US)

(73) Assignee: Stackhouse, Inc., Yorba Linda, CA (US)

( * ) Notice: Subject to any disclaimer, the term of this patent is extended or adjusted under 35 U.S.C. 154(b) by 0 days.

(21) Appl. No.: 09/531,948

(22) Filed: Mar. 21, 2000

(51) Int. Cl.$^7$ .......................... B01D 46/00; B01D 46/46

(52) U.S. Cl. ............................ 96/417; 96/421; 96/422; 96/424; 95/19; 95/23; 95/25; 95/26; 55/DIG. 34

(58) Field of Search .......................... 96/397, 417, 421, 96/422, 424; 55/385.1, 385.2, 467, 471, DIG. 34; 95/19, 22, 23, 25, 26, 273

(56) References Cited

U.S. PATENT DOCUMENTS

| | | |
|---|---|---|
| 2,096,484 A | 10/1937 | Farmer |
| 2,565,764 A | 8/1951 | Flanagan |
| 2,804,075 A | 8/1957 | Borden |
| 2,825,424 A | 3/1958 | Gross |
| 3,012,322 A | 12/1961 | Thompson |
| 3,736,927 A | 6/1973 | Misagi |
| 3,742,947 A | 7/1973 | Hashem |
| 4,019,508 A | 4/1977 | Der Estephanian et al. |
| 4,050,291 A * | 9/1977 | Nelson .......................... 96/421 |
| 4,055,173 A | 10/1977 | Knab |
| 4,064,876 A | 12/1977 | Mulchi |
| 4,207,887 A | 6/1980 | Hiltebrandt et al. |
| 4,236,902 A | 12/1980 | Fricke |
| 4,294,251 A | 10/1981 | Greenwald et al. |
| 4,549,542 A | 10/1985 | Chien |
| 4,619,672 A | 10/1986 | Robertson |
| 4,619,675 A | 10/1986 | Watanabe |
| 4,648,386 A | 3/1987 | Morritt et al. |
| 4,687,579 A | 8/1987 | Bergman |
| 4,715,372 A | 12/1987 | Philippbar et al. |
| 4,719,914 A | 1/1988 | Johnson |
| 4,735,603 A | 4/1988 | Goodson et al. |
| 4,735,606 A | 4/1988 | Davison |
| 4,781,021 A | 11/1988 | Winberg |
| 4,784,675 A * | 11/1988 | Leber et al. .................. 96/421 |
| 4,786,295 A * | 11/1988 | Newman et al. .............. 96/421 |
| 4,810,269 A | 3/1989 | Stackhouse et al. |
| 4,826,513 A | 5/1989 | Stackhouse et al. |
| 4,850,352 A | 7/1989 | Johnson |
| 4,853,772 A | 8/1989 | Kikuchi |
| D304,612 S | 11/1989 | Stackhouse et al. |
| 4,900,344 A | 2/1990 | Lansing |
| 4,931,047 A | 6/1990 | Broadwin et al. |

(List continued on next page.)

FOREIGN PATENT DOCUMENTS

GB    2078128 A    1/1982

*Primary Examiner*—Duane Smith
*Assistant Examiner*—Jason M. Greene
(74) *Attorney, Agent, or Firm*—Stetina Brunda Garred & Brucker

(57) ABSTRACT

A filtration system for trapping airborne contaminants as exemplified in evacuating smoke generated during a surgical procedure wherein operation efficiency thereof is automatically reported in relation to filter structure cumulative use time and cumulative airflow volume. In a first embodiment a system processor correlates cumulative vacuum pump motor speed, operation duration, and air pressure difference measurements over an airflow filter path into a cumulative value and automatically compares that value to a plurality of known pre-determined correlated values to thereby provide filter life expectancy which is conveyed to a memory device of the filter structure for retention and conveyance for display. In a second embodiment a self-contained microprocessor and memory device of the filter structure is in communication with the system processor to receive, store, and send filter structure time-duration operability data which is sent to a data display site for display.

10 Claims, 3 Drawing Sheets

U.S. PATENT DOCUMENTS

| | | |
|---|---|---|
| 4,957,492 A | 9/1990 | McVay |
| 4,963,134 A | 10/1990 | Backscheider et al. |
| 4,966,578 A | 10/1990 | Baier et al. |
| 4,971,034 A | 11/1990 | Doi et al. |
| 4,983,901 A | 1/1991 | Lehmer |
| 4,986,839 A | 1/1991 | Wertz et al. |
| 5,013,294 A | 5/1991 | Baier |
| 5,047,072 A | 9/1991 | Wertz et al. |
| 5,076,787 A | 12/1991 | Overmyer |
| 5,085,657 A | 2/1992 | Ben-Simhon |
| 5,088,997 A | 2/1992 | Delahuerga et al. |
| 5,108,389 A | 4/1992 | Cosmescu |
| 5,160,334 A | 11/1992 | Billings et al. |
| 5,199,944 A | 4/1993 | Cosmescu |
| 5,226,939 A | 7/1993 | Nicolas et al. |
| 5,242,404 A | 9/1993 | Conley et al. |
| 5,318,516 A | 6/1994 | Cosmescu |
| 5,456,248 A | 10/1995 | Holian et al. |
| 5,461,368 A * | 10/1995 | Comer |
| 5,520,668 A | 5/1996 | Greff et al. |
| 5,580,347 A | 12/1996 | Reimels |
| 5,606,311 A * | 2/1997 | Polidan et al. ............ 96/421 |
| 5,620,441 A | 4/1997 | Greff et al. |
| 5,674,381 A * | 10/1997 | Den Dekker ............ 96/417 |
| 5,810,908 A * | 9/1998 | Gray et al. |
| 5,853,410 A | 12/1998 | Greff et al. |
| 6,030,437 A * | 2/2000 | Gourrier et al. |
| 6,040,777 A * | 3/2000 | Ammann et al. ............ 95/25 |
| 6,203,590 B1 * | 3/2001 | Byrd et al. ............ 96/422 |

* cited by examiner

AIR FILTRATION SYSTEM WITH FILTER EFFICIENCY MANAGEMENT

CROSS-REFERENCE TO RELATED APPLICATIONS (Not Applicable)

STATEMENT RE: FEDERALLY SPONSORED RESEARCH/DEVELOPMENT (Not Applicable)

1. Field of the Invention

The present invention relates in general to air filtration systems, and in particular to an air filtration system employable for evacuating smoke generated during a surgical procedure and including a replaceable filter structure thereof provided with filter efficiency measurement selected from (1) a memory device integral with the filter structure and capable of storing and displaying remaining time duration operability data for the filter structure, and (2) a self-contained microprocessor and memory device integral with the filter structure and capable of calculating, storing, and displaying remaining time duration operability data for the filter structure.

2. Background of the Invention

Filtration of airborne contaminants is extremely important where such contaminants have the potential of causing both short-term and long-term health hazards to those who would be exposed to breathing and/or otherwise contacting the untoward components in the air so filtered. One exemplary, but non-limiting, environment where potentially dangerous contaminants may be present is found in a surgical theater where patient tissue is exposed to electro-surgical excision, cauterization, or like heat producing treatments that cause smoke having tissue particulate therewith to emanate from the treatment site and enter the immediate atmosphere. Such particulate can be especially dangerous if its origin is from disease-containing tissue and if that particulate has a tendency to retain disease-transference capabilities.

The necessity for filtration systems to be able to effectively remove airborne particulate, including that found in smoke produced by burning tissue during a surgical procedure, is recognized in the prior art. For example, U.S. Pat. No. 4,810,269 to Stackhouse, et al., U.S. Pat. No. 5,226,939 to Nicolas et al., and U.S. Pat. No. 5,456,248 to Holian et al. all teach variously configured mobile filtration systems capable of removing extremely small particles present in smoke generated during such heat-producing surgical procedures.

At the heart of any filtration system is, of course, the effectiveness of its filter medium. Of particular importance is the ability of any filtration medium to be able to perform adequately in the removal of untoward contaminants. Thus, for example, if a filter medium becomes inundated with particulate, it can become at least partially blocked and therefore may not be adequately efficient in removing potentially toxic particulate. Therefore, it is extremely important that the condition of the filter medium be known when the filtration system with which it is associated is activated so that fully effective particulate removal can occur. One primary indicator that relates to filter medium effectiveness is the cumulative length of time the filter medium has been in use. For example, experience with a particular filter structure may show that such filter structure has a cumulative useful life of about 20 minutes. However, unless the burdensome task of maintaining a written detailed log of operation time is undertaken, a surgical team member must guess an approximation of filtration effectiveness remaining in the filtration system.

While automatic measurement of operating time can be incorporated into system operation, there is yet another factor that also determines filter life and filter efficiency. That factor is the volume of air that has passed through the filter medium. Thus, if the above noted filter is in operation for 20 minutes at a low airflow rate, it may still have filtering capability. Conversely, if the same filter in operation for only 10 minutes at a very high airflow rate, it may not possess proper efficiency.

In view of the above described criticality of filtration efficiency, it is apparent that a need is present for providing immediate filtration capability information in relation to system operation. Accordingly, a primary object of the present invention is to provide correlated cumulative time-sensitive and airflow volume information directly to the user relative to filter structure and remaining life.

Another object of the present invention is to provide such information as a visual display of time remaining for effective use.

Yet another object of the present invention is to provide an audible warning when unacceptable filter medium performance is expected in view of time and airflow volume correlations.

These and other objects of the present invention will become apparent throughout the description thereof which now follows.

BRIEF SUMMARY OF THE INVENTION

The present invention is a filtration system for trapping airborne contaminants wherein operation efficiency thereof is automatically reported in relation to filter structure cumulative use time and airflow volume. An application of use of the system is exemplified in evacuating smoke generated during a surgical procedure such as electrosurgery, cauterization, and the like to thereby entrap potentially hazardous particulate emanating from treated tissue and residing in the smoke. The system includes a housing with an airflow channel therethrough having an air entry port and an air exit port, a vacuum production device for drawing air through the airflow channel, a variable speed motor operating the vacuum production device, and air pressure measuring apparatus disposed at the air entry and air exit ports for measuring air pressure difference between entry and exit ports, and a data display site for displaying remaining time duration operability data. An audible alarm can be included for warning users of untoward filter medium conditions.

In a first preferred embodiment, the system comprises a system processor for receiving and processing data. The system processor is in communication with the variable speed motor for receiving motor speed and operation duration data and in communication with the air pressure measuring apparatus for receiving air pressure difference measurement to thereby correlate cumulative motor speed, operation duration, and air pressure difference measurements into a cumulative time and filtered-air volume operating correlated value and automatically comparing that operating correlated value to a plurality of known pre-determined correlated values each reflecting remaining time duration operability of a replaceable filter structure at one respective pre-determined correlated value. The replaceable filter structure, which is disposed in the airflow channel for capturing airborne contaminants, has at least one filtration medium, and is provided with a memory device in communication with the system processor for receiving and storing remaining time duration operability data and for sending this remaining time duration operability data from the filter structure to the system processor for display at the data display site.

In a second preferred embodiment, the system comprises a filter structure comprising, once again, at least one filtration medium. The filter structure additionally comprises a self-contained microprocessor and memory device in communication with the variable speed motor for receiving motor speed and operation duration data and in communication with the air pressure measuring apparatus for receiving air pressure difference measurement to thereby correlate cumulative motor speed, operation duration, and air pressure difference measurements into an operating cumulative time and filtered-air volume correlated value and automatically comparing that operating correlated value to a plurality of known pre-determined correlated values each reflecting remaining time duration operability of a replaceable filter structure at one respective pre-determined correlated value to determine remaining time duration operability of the filter structure. This remaining time duration operability data is then sent from the microprocessor and memory device of the filter structure to a data display site for display.

The invention includes the filter structure having a memory device only as related in the first preferred embodiment, and the filter structure having a self-contained microprocessor and memory device as related in the second preferred embodiment. As is thus apparent, filtration system efficiency is monitored so that the system can be effective in maintaining a safe operation site.

BRIEF DESCRIPTION OF THE SEVERAL VIEWS OF THE DRAWING

An illustrative and presently preferred embodiment of the invention is shown in the accompanying drawings in which.

DETAILED DESCRIPTION OF THE INVENTION

Figure 1:
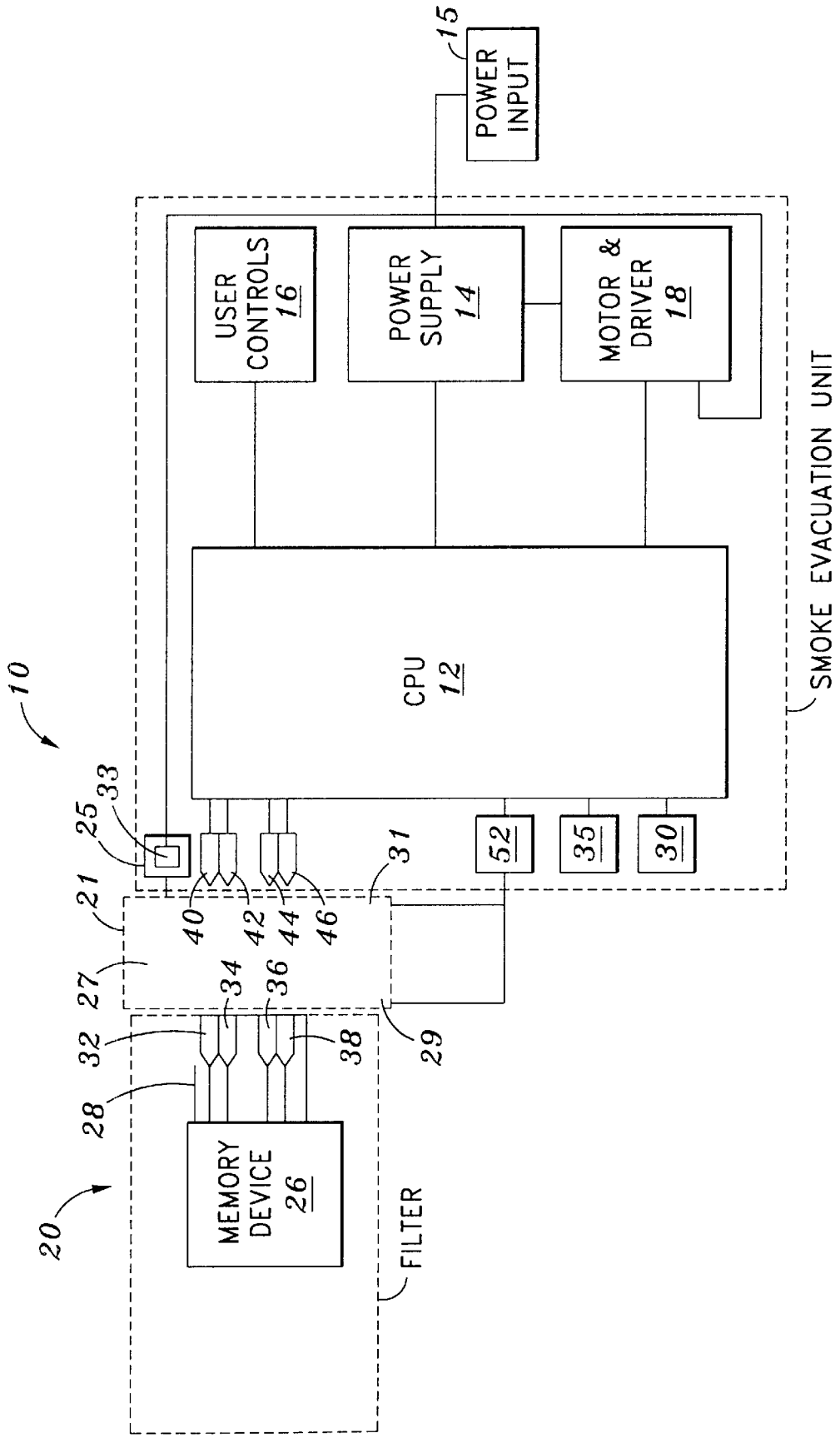
FIG. 1 is a schematic view of a first embodiment of a smoke evacuation filtration system.
Figure 4:
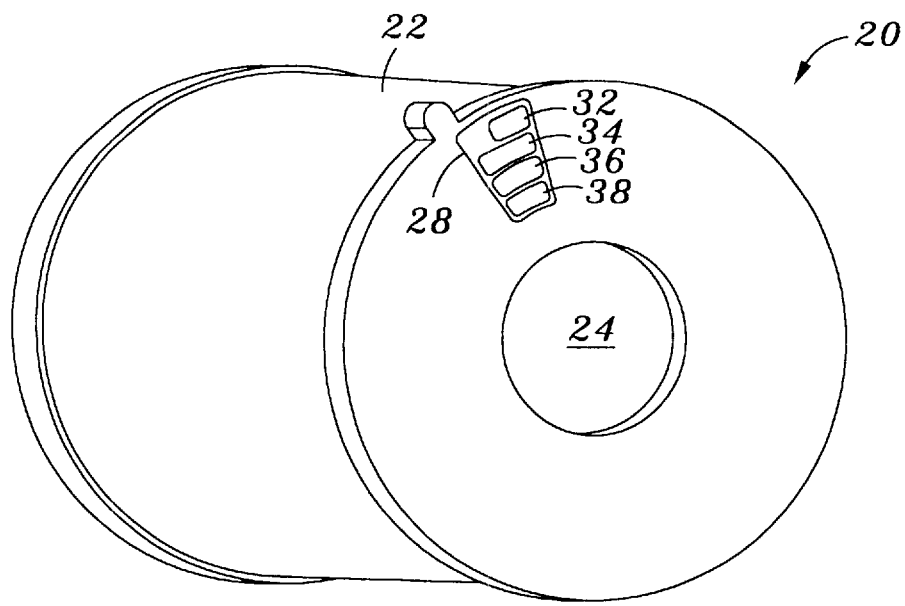
FIG. 4 is a perspective view of a filter structure.

Referring to FIG. 1, a first embodiment of a smoke evacuation filtration system 10 is illustrated. The system 10 includes a system processor 12 in conventional communication with a power supply. 14 connected to a power input 15, user controls 16, and a motor/driver unit 18 that operates a conventional variable speed motor 33 of a standard vacuum pump 25 for conventionally drawing air for filtration through the system 10. Air filtration is effectuated through a filter structure 20 placed within an airflow channel 27 of a housing 21 of the system 10. In particular, and as shown in FIG. 4, the filter structure 20 can be a drum configuration with a filter medium 22 preferably able to remove ultra-small airborne contaminant with high efficiency from air drawn through the medium 22 for exit through the opening 24 in direct access to the vacuum air draw. The airflow channel 27 has. an air entry port 29 and an air exit port 31 bridged by a conventional pressure transducer 52 for measuring the air pressure at the exit port 31 just prior to the vacuum pump 25. As shown in FIG. 1, the system processor 12 is in communication with the pressure transducer 52 to process pressure measurement data therefrom, and also in communication with the variable speed motor 33 of the vacuum pump 25 to process motor speed data. A data display site 30 is provided for user reference.

Figure 3:
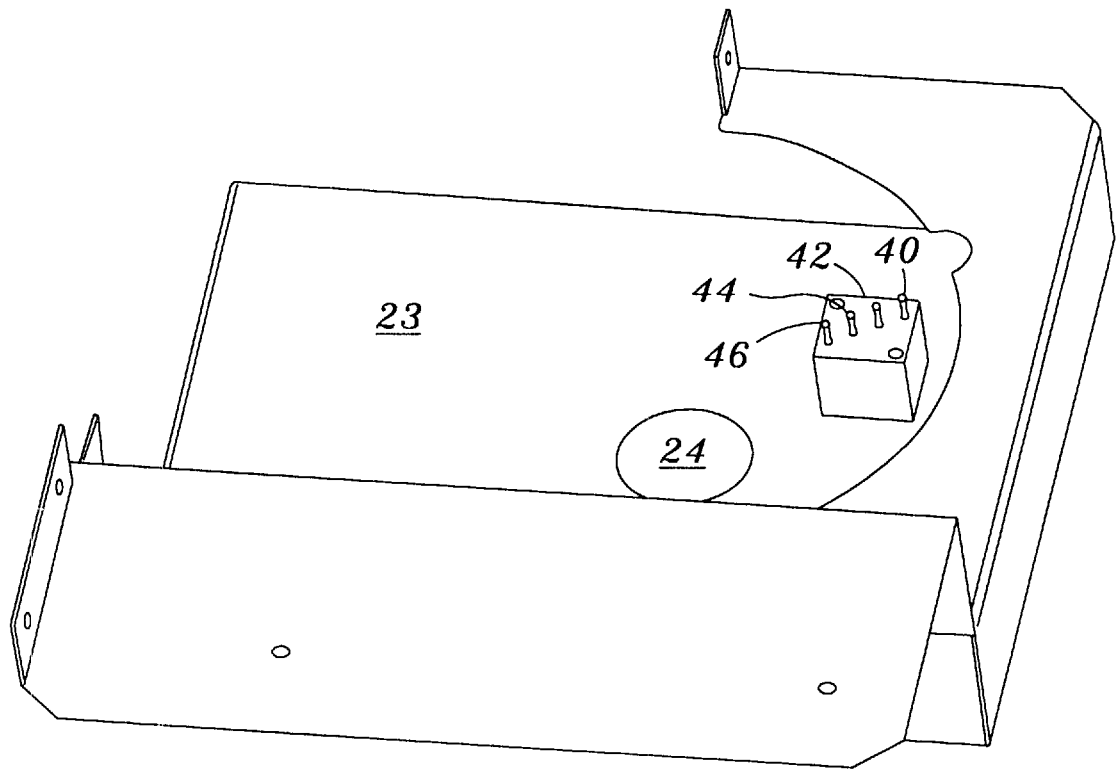
FIG. 3 is a perspective view of a filtration system mount for a filter structure.

The filter structure 20 of the embodiment of FIG. 1 additionally includes a standard non-volatile memory device 26, preferably capable of storing at least 256 bytes of data, for storing data as described below for the filter structure 20 and for sending this data through a control conduit 28 from the filter structure 20 to the system processor 12 for display at the data display site 30. As shown in FIGS. 1, 3, and 4, the control conduit 28 includes a power trace 32, ground trace 34, clock trace 36, and data trace 38 which, when the filter structure 20 is plugged into the system 10, make electrical contact with four respective counterpart connectors 40, 42, 44, 46 leading from the system processor 12. Connection is accomplished by placing the filter structure 22 into a mount 23, shown in FIG. 3, which is disposed within the airflow channel 27.

In operation, the system processor 12 controls vacuum pump motor speed and receives operation duration data and air pressure difference measurement from the pressure transducer 52 to thereby correlate cumulative motor speed, operation duration, and air pressure difference measurements into a cumulative time and filtered-air volume operating correlated value. This value is then compared to a plurality of known pre-determined correlated values each reflecting remaining time duration operability of a replaceable filter structure at one such respective pre-determined correlated value to thereby produce a remaining time duration operability value for the filter structure 20. The memory device 26 is in communication with the system processor 12 for receiving and storing remaining time duration operability data so calculated by the system processor 12. This information, which is unique to the particular filter structure 20, is sent from the memory device 26 to the system processor 12 for display at the data display site 30 to thereby convey useful filter structure life irrespective of the system with which it is associated. Additionally, a standard audible signal producer 35 such as a horn or bell can be provided to sound when filter life is dangerously low or fully spent. In this manner filter structures can be moved from machine to machine without loss of filter effectiveness measurement.

Figure 2:
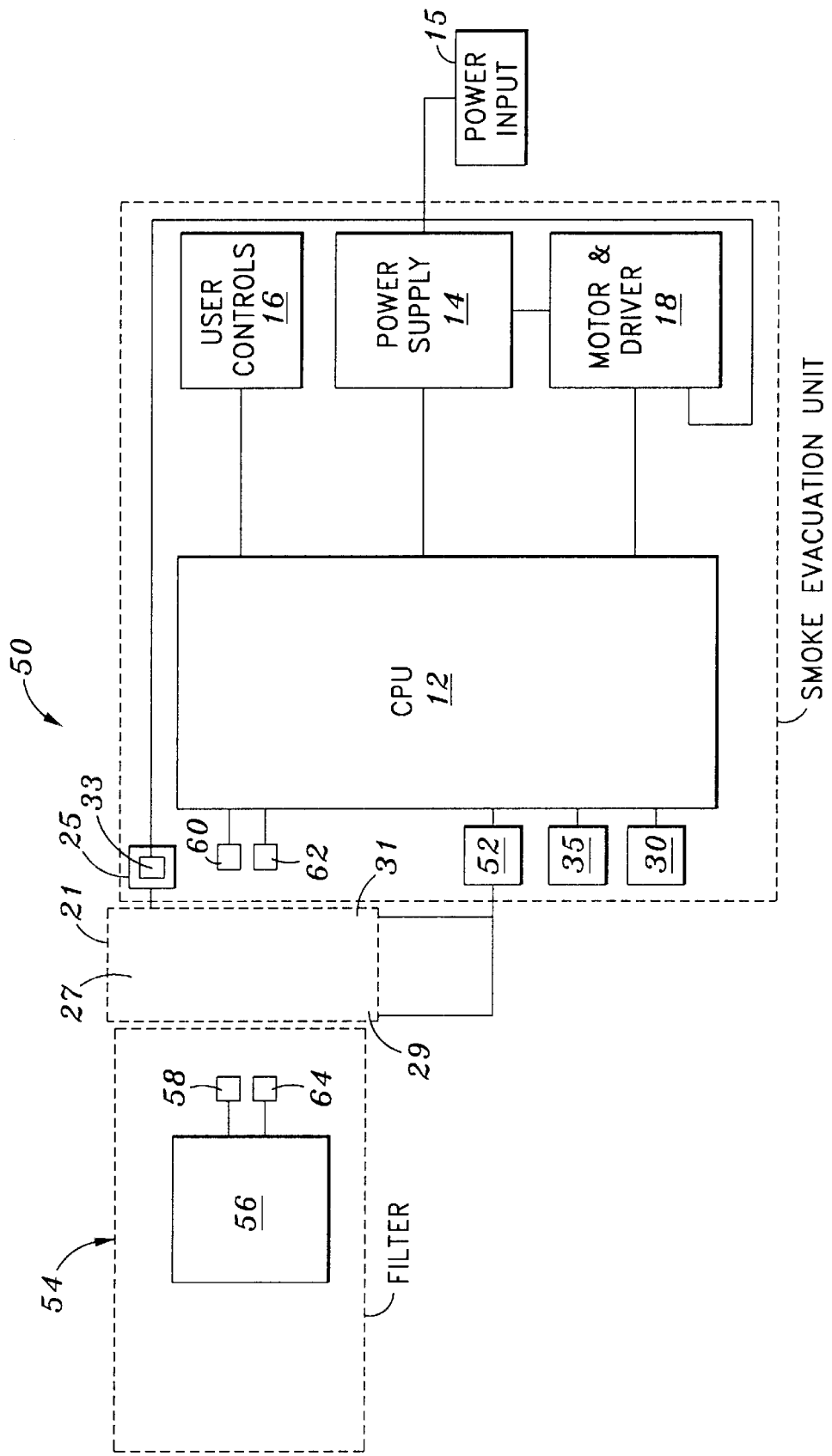
FIG. 2 is a schematic view of a second embodiment of a smoke evacuation filtration system.

FIG. 2 illustrates a second embodiment of a smoke evacuation filtration system 50. The system 50 includes a system processor 12 in conventional communication with a power supply 14 connected to a power input 15, user controls 16, and a motor driver unit 18 that operates a conventional variable speed motor 33 of a standard vacuum pump 25 for conventionally drawing air for filtration through the system 10. Air filtration is effectuated through a filter structure 54 placed within an airflow channel 27 of a housing 21 of the system 50. The airflow channel 27 has an air entry port 29 and an air exit port 31 bridged by a conventional pressure transducer 52 for measuring the air pressure at the exit port 31 just before the motor intake. A data display site 30 is provided for user reference.

The filter structure 54 of the embodiment of FIG. 2 additionally includes a self-contained battery-powered microprocessor and memory device 56, preferably having a conventional sleep-mode default with activation upon data input and preferably capable of storing at least 20 bytes of data, for receiving, processing, storing, and sending data as described below. As shown in FIG. 2, communication between the system processor 12 and the device 56 is accomplished optically, first from the device 56 through a conventional transmitter 58 to a conventional receiver 60 of the system processor 12, and second from the system processor 12 through a transmitter 62 to a receiver 64 of the device 56.

In operation, the system processor 12 controls vacuum pump motor speed, and receives operation duration data and air pressure difference measurement from the pressure transducer 52 and transmits this information to the microprocessor and memory device 56 of the filter structure 54. The microprocessor component 12 of the device 56 then correlates cumulative motor speed, operation duration, and air pressure difference measurements into a cumulative time and filtered-air volume operating correlated value. This value is then compared to a plurality of known pre-determined correlated values each reflecting remaining time duration operability of a replaceable filter structure at one such respective pre-determined correlated value to thereby produce a remaining time duration operability value for the filter structure 54. This information, which is unique to the particular filter structure 54, is sent from the device 56 to the system processor 12 for display at the data display site 30 to thereby convey useful filter structure life. Additionally, a standard audible signal producer 35 such as a horn or bell can be provided to sound when filter life is dangerously low or fully spent. As is thus apparent, the filter structure 54 is capable of continually updating its remaining life, irrespective of the filtration system 50 with which it is associated.

As is evident, the above-described filtration systems function to maintain safe ambient conditions through operation enablement in accord with reporting filtration capabilities for the removal of airborne contaminants. While illustrative and presently preferred embodiments of the invention have been described in detail herein, it is to be understood that the inventive concepts may be otherwise variously embodied and employed and that the appended claims are intended to be construed to include such variations except insofar as limited by the prior art.

What is claimed is:

1. A filtration system for trapping airborne contaminants, said filtration system comprising:
    a) a housing with an airflow channel therethrough having an air entry port and an air exit port;
    b) a vacuum production device for drawing air through said airflow channel;
    c) a variable speed motor operating the vacuum production device;
    d) air pressure measuring apparatus disposed at the air exit port for measuring air pressure at said port, upstream from the motor;
    e) a system processor for receiving and processing data, said system processor in communication with the variable speed motor for controlling motor speed and receiving operation duration data and in communication with the air pressure measuring apparatus for receiving air pressure difference measurement to thereby correlate cumulative motor speed, operation duration, and air pressure difference measurements into a cumulative time and filtered-air volume operating correlated value and automatically comparing said operating correlated value to a plurality of known pre-determined correlated values each reflecting remaining time duration operability of a replaceable filter structure at one respective pre-determined correlated value;
    f) a data display site in communication with the system processor for displaying data from said system processor; and
    g) a replaceable filter structure disposed in the airflow channel for capturing airborne contaminants, said filter structure comprising at least one filtration medium for capturing airborne contaminant, and a memory device in communication with the system processor for receiving and storing remaining time duration operability data and for sending said remaining time duration operability data from the filter structure to the system processor for display at said data display site.

2. A filtration system as claimed in claim 1 wherein the air pressure measuring apparatus is a pressure transducer.

3. A filtration system as claimed in claim 1 wherein the memory device is in electrical communication with the system processor.

4. A filtration system as claimed in claim 1 additionally comprising an audible signal for providing a warning of a correlated value exceeding an acceptable level.

5. A replaceable filter structure for use within a filtration system for trapping airborne contaminants and positionable within an airflow channel of the filtration system through which air to be filtered travels, the filter structure comprising:
    a) at least one filtration medium; and
    b) a memory device connectable with a system processor of the filtration system for receiving, storing, and reporting remaining time duration operability of said replaceable filter structure, said remaining time duration operability correlated and determined by said system processor from past cumulative motor speed, operation duration, and air pressure difference measurements.

6. A replaceable filter structure as claimed in claim 5 wherein the memory device is electrically connectable with said system processor.

7. A filtration system for trapping airborne contaminants, said filtration system comprising:
    a) a housing with an airflow channel therethrough having an air entry port and an air exit port;
    b) a vacuum production device for drawing air through said airflow channel;
    c) a variable speed motor operating the vacuum production device;
    d) air pressure measuring apparatus disposed at the air entry and air exit ports for measuring air pressure difference between said ports;
    e) a data display site; and
    f) a replaceable filter structure disposed in the airflow channel for capturing airborne contaminants, said filter structure comprising:
        i) at least one filtration medium; and
        ii) a self-contained microprocessor and memory device in communication with the variable speed motor for receiving motor speed and operation duration data and in communication with the air pressure measuring apparatus for receiving air pressure difference measurement to thereby correlate cumulative motor speed, operation duration, and air pressure difference measurements into an operating cumulative time and filtered-air volume correlated value and automatically comparing said operating correlated value to a plurality of known pre-determined correlated values each reflecting remaining time duration operability of a replaceable filter structure at one respective pre-determined correlated value to determine remaining time duration operability of said filter structure, and for sending said remaining time duration operability data from the filter structure to a data display site for display.

8. A filtration system as claimed in claim 7 wherein the air pressure measuring apparatus is a pressure transducer.

9. A filtration system as claimed in claim 7 wherein communication of the microprocessor and memory device is optical communication.

10. A filtration system as claimed in claim 7 additionally comprising an audible signal for providing a warning of non-acceptable remaining time duration operability data.

* * * * *